(12) United States Patent
Buice et al.

(10) Patent No.: US 8,914,088 B2
(45) Date of Patent: Dec. 16, 2014

(54) MEDICAL SENSOR AND TECHNIQUE FOR USING THE SAME

(75) Inventors: Carl Buice, Boulder, CO (US); Edward McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1334 days.

(21) Appl. No.: 12/241,260

(22) Filed: Sep. 30, 2008

(65) Prior Publication Data
US 2010/0081901 A1     Apr. 1, 2010

(51) Int. Cl.
*A61B 5/00* (2006.01)
*A61B 5/1455* (2006.01)

(52) U.S. Cl.
CPC ......... *A61B 5/14551* (2013.01); *A61B 5/14552* (2013.01); *A61B 5/6826* (2013.01); *A61B 5/6838* (2013.01); *A61B 5/0059* (2013.01)
USPC ............................. 600/310; 600/322; 600/323

(58) Field of Classification Search
USPC ......... 600/322, 323, 329, 330, 331, 336, 337, 600/340, 310, 22
See application file for complete search history.

(56) References Cited

U.S. PATENT DOCUMENTS

| | | | |
|---|---|---|---|
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |

(Continued)

FOREIGN PATENT DOCUMENTS

| | | |
|---|---|---|
| DE | 19640807 | 9/1997 |
| EP | 0724860 | 8/1996 |

(Continued)

OTHER PUBLICATIONS

Lutter, N., et al.; "Comparison of Different Evaluation Methods for a Multi-wavelength Pulse Oximeter," *Biomedizinische Technik*, vol. 43, (1998).

(Continued)

*Primary Examiner* — Jeffrey G Hoekstra
*Assistant Examiner* — Megan Leedy
(74) *Attorney, Agent, or Firm* — Fletcher Yoder PC

(57) ABSTRACT

According to embodiments, sensors and systems for medical spectroscopy may include adaptive optical components, such as digital light processing components. Adaptive light emitting elements may allow such sensors to alter the intensity profile of emitted light photons to change the distribution of photons through the tissue or to scan areas of tissue to determine if certain areas may be associated with improved measurements. In addition, sensors with adaptive light detecting elements as provided may adapt to selectively detect light of certain wavelengths or from certain regions of the tissue.

9 Claims, 7 Drawing Sheets

(56) References Cited

U.S. PATENT DOCUMENTS

| | | |
|---|---|---|
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A * | 9/1993 | Prosser ..................... 600/336 |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |

(56) References Cited

U.S. PATENT DOCUMENTS

| | | |
|---|---|---|
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |

(56) References Cited

U.S. PATENT DOCUMENTS

| | | |
|---|---|---|
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllerman et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,369,954 B1 | 4/2002 | Berge et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |

(56) References Cited

U.S. PATENT DOCUMENTS

| | | |
|---|---|---|
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,127 B2 | 12/2003 | Bao et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,711,426 B2 | 3/2004 | Benaron et al. |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,792,300 B1 | 9/2004 | Diab et al. |
| 6,793,654 B2 | 9/2004 | Lemberg |
| 6,801,797 B2 | 10/2004 | Mannheimer et al. |

(56) References Cited

U.S. PATENT DOCUMENTS

| | | | |
|---|---|---|---|
| 6,801,798 B2 | 10/2004 | Geddes et al. | |
| 6,801,799 B2 | 10/2004 | Mendelson | |
| 6,801,802 B2 | 10/2004 | Sitzman et al. | |
| 6,802,812 B1 * | 10/2004 | Walker et al. | 600/309 |
| 6,805,673 B2 | 10/2004 | Dekker | |
| 6,810,277 B2 | 10/2004 | Edgar, Jr. et al. | |
| 6,813,511 B2 | 11/2004 | Diab et al. | |
| 6,816,266 B2 | 11/2004 | Varshneya et al. | |
| 6,816,741 B2 | 11/2004 | Diab | |
| 6,819,950 B2 | 11/2004 | Mills | |
| 6,822,564 B2 | 11/2004 | Al-Ali | |
| 6,825,619 B2 | 11/2004 | Norris | |
| 6,826,419 B2 | 11/2004 | Diab et al. | |
| 6,829,496 B2 | 12/2004 | Nagai et al. | |
| 6,830,711 B2 | 12/2004 | Mills et al. | |
| 6,836,679 B2 | 12/2004 | Baker, Jr. et al. | |
| 6,839,579 B1 | 1/2005 | Chin | |
| 6,839,580 B2 | 1/2005 | Zonios et al. | |
| 6,839,582 B2 | 1/2005 | Heckel | |
| 6,839,659 B2 | 1/2005 | Tarassenko et al. | |
| 6,842,635 B1 | 1/2005 | Parker | |
| 6,845,256 B2 | 1/2005 | Chin et al. | |
| 6,850,787 B2 | 2/2005 | Weber et al. | |
| 6,850,788 B2 | 2/2005 | Al-Ali | |
| 6,850,789 B2 | 2/2005 | Schweitzer, Jr. et al. | |
| 6,861,639 B2 | 3/2005 | Al-Ali | |
| 6,862,091 B2 | 3/2005 | Johnson | |
| 6,863,652 B2 | 3/2005 | Huang et al. | |
| 6,865,407 B2 | 3/2005 | Kimball et al. | |
| 6,879,850 B2 | 4/2005 | Kimball | |
| 6,882,874 B2 | 4/2005 | Huiku | |
| 6,889,153 B2 | 5/2005 | Dietiker | |
| 6,898,452 B2 | 5/2005 | Al-Ali et al. | |
| 6,909,912 B2 | 6/2005 | Melker et al. | |
| 6,912,413 B2 | 6/2005 | Rantala et al. | |
| 6,916,289 B2 | 7/2005 | Schnall | |
| 6,920,345 B2 | 7/2005 | Al-Ali et al. | |
| 6,931,269 B2 | 8/2005 | Terry | |
| 6,934,570 B2 | 8/2005 | Kiani et al. | |
| 6,939,307 B1 | 9/2005 | Dunlop | |
| 6,941,162 B2 | 9/2005 | Fudge et al. | |
| 6,947,781 B2 | 9/2005 | Asada et al. | |
| 6,950,687 B2 | 9/2005 | Al-Ali | |
| 6,963,767 B2 | 11/2005 | Rantala et al. | |
| 6,971,580 B2 | 12/2005 | DeLonzor et al. | |
| 6,983,178 B2 | 1/2006 | Fine et al. | |
| 6,985,763 B2 | 1/2006 | Boas et al. | |
| 6,985,764 B2 | 1/2006 | Mason et al. | |
| 6,990,426 B2 | 1/2006 | Yoon et al. | |
| 6,992,751 B2 | 1/2006 | Okita et al. | |
| 6,992,772 B2 | 1/2006 | Block et al. | |
| 6,993,371 B2 | 1/2006 | Kiani et al. | |
| 6,993,372 B2 | 1/2006 | Fine et al. | |
| 6,996,427 B2 | 2/2006 | Ali et al. | |
| 7,003,338 B2 | 2/2006 | Weber et al. | |
| 7,003,339 B2 | 2/2006 | Diab et al. | |
| 7,006,855 B1 | 2/2006 | Sarussi | |
| 7,006,856 B2 | 2/2006 | Baker, Jr. et al. | |
| 7,016,715 B2 | 3/2006 | Stetson | |
| 7,020,507 B2 | 3/2006 | Scharf et al. | |
| 7,024,233 B2 | 4/2006 | Ali et al. | |
| 7,024,235 B2 | 4/2006 | Melker et al. | |
| 7,025,728 B2 | 4/2006 | Ito et al. | |
| 7,027,849 B2 | 4/2006 | Al-Ali et al. | |
| 7,027,850 B2 | 4/2006 | Wasserman | |
| 7,035,697 B1 | 4/2006 | Brown | |
| 7,039,449 B2 | 5/2006 | Al-Ali | |
| 7,043,289 B2 | 5/2006 | Fine et al. | |
| 7,047,055 B2 | 5/2006 | Boas et al. | |
| 7,047,056 B2 | 5/2006 | Hannula et al. | |
| 7,060,035 B2 | 6/2006 | Wasserman et al. | |
| 7,062,306 B2 | 6/2006 | Benaron et al. | |
| 7,062,307 B2 | 6/2006 | Norris et al. | |
| 7,065,392 B2 * | 6/2006 | Kato | 600/323 |
| 7,067,893 B2 | 6/2006 | Mills et al. | |
| 7,072,701 B2 | 7/2006 | Chen et al. | |
| 7,072,702 B2 | 7/2006 | Edgar, Jr. et al. | |
| 7,079,880 B2 | 7/2006 | Stetson | |
| 7,085,597 B2 | 8/2006 | Fein et al. | |
| 7,096,052 B2 | 8/2006 | Mason et al. | |
| 7,096,054 B2 | 8/2006 | Abdul-Hafiz et al. | |
| 7,107,088 B2 | 9/2006 | Aceti | |
| 7,107,116 B2 | 9/2006 | Geng | |
| 7,113,815 B2 | 9/2006 | O'Neil et al. | |
| 7,123,950 B2 | 10/2006 | Mannheimer | |
| 7,127,278 B2 | 10/2006 | Melker et al. | |
| 7,130,671 B2 | 10/2006 | Baker, Jr. et al. | |
| 7,130,672 B2 | 10/2006 | Pewzner et al. | |
| 7,132,641 B2 | 11/2006 | Schulz et al. | |
| 7,133,711 B2 | 11/2006 | Chernoguz et al. | |
| 7,134,754 B2 | 11/2006 | Kerr | |
| 7,139,599 B2 | 11/2006 | Terry | |
| 7,142,901 B2 | 11/2006 | Kiani et al. | |
| 7,149,293 B1 | 12/2006 | Coppage et al. | |
| 7,162,288 B2 | 1/2007 | Nordstrom | |
| 7,190,987 B2 | 3/2007 | Lindekugel et al. | |
| 7,198,778 B2 | 4/2007 | Achilefu et al. | |
| 7,209,775 B2 | 4/2007 | Bae et al. | |
| 7,215,984 B2 | 5/2007 | Diab et al. | |
| 7,221,969 B2 | 5/2007 | Stoddart et al. | |
| 7,225,006 B2 | 5/2007 | Al-Ali et al. | |
| 7,236,811 B2 | 6/2007 | Schmitt | |
| 7,242,997 B2 | 7/2007 | Geng | |
| 7,248,910 B2 | 7/2007 | Li et al. | |
| 7,254,433 B2 | 8/2007 | Diab et al. | |
| 7,254,434 B2 | 8/2007 | Schulz et al. | |
| 7,263,395 B2 | 8/2007 | Chan et al. | |
| 7,272,426 B2 | 9/2007 | Schmid | |
| 7,280,858 B2 | 10/2007 | Al-Ali et al. | |
| 7,283,242 B2 | 10/2007 | Thornton | |
| 7,295,866 B2 | 11/2007 | Al-Ali et al. | |
| 7,305,262 B2 | 12/2007 | Brodnick et al. | |
| 7,315,753 B2 | 1/2008 | Baker, Jr. et al. | |
| 7,356,365 B2 | 4/2008 | Schurman | |
| 7,389,131 B2 * | 6/2008 | Kanayama | 600/322 |
| 2001/0021803 A1 | 9/2001 | Blank et al. | |
| 2001/0051767 A1 | 12/2001 | Williams et al. | |
| 2002/0026109 A1 | 2/2002 | Diab et al. | |
| 2002/0028990 A1 | 3/2002 | Shepherd et al. | |
| 2002/0038078 A1 | 3/2002 | Ito | |
| 2002/0042558 A1 | 4/2002 | Mendelson | |
| 2002/0068859 A1 | 6/2002 | Knopp | |
| 2002/0128544 A1 | 9/2002 | Diab et al. | |
| 2002/0133067 A1 | 9/2002 | Jackson, III | |
| 2002/0156354 A1 | 10/2002 | Larson | |
| 2002/0173706 A1 | 11/2002 | Takatani | |
| 2002/0173709 A1 | 11/2002 | Fine et al. | |
| 2002/0190863 A1 | 12/2002 | Lynn | |
| 2002/0198442 A1 | 12/2002 | Rantala et al. | |
| 2003/0018243 A1 | 1/2003 | Gerhardt et al. | |
| 2003/0036690 A1 | 2/2003 | Geddes et al. | |
| 2003/0045785 A1 | 3/2003 | Diab et al. | |
| 2003/0073889 A1 | 4/2003 | Keilbach et al. | |
| 2003/0073890 A1 | 4/2003 | Hanna | |
| 2003/0100840 A1 | 5/2003 | Sugiura et al. | |
| 2003/0132495 A1 | 7/2003 | Mills et al. | |
| 2003/0135099 A1 | 7/2003 | Al-Ali | |
| 2003/0162414 A1 | 8/2003 | Schulz et al. | |
| 2003/0171662 A1 | 9/2003 | O'Connor et al. | |
| 2003/0176776 A1 | 9/2003 | Huiku | |
| 2003/0181799 A1 | 9/2003 | Lindekugel et al. | |
| 2003/0187337 A1 | 10/2003 | Tarassenko et al. | |
| 2003/0195402 A1 | 10/2003 | Fein et al. | |
| 2003/0197679 A1 | 10/2003 | Ali et al. | |
| 2003/0212316 A1 | 11/2003 | Leiden et al. | |
| 2003/0225323 A1 | 12/2003 | Kiani et al. | |
| 2003/0225337 A1 | 12/2003 | Scharf et al. | |
| 2003/0236452 A1 | 12/2003 | Melker et al. | |
| 2003/0236647 A1 | 12/2003 | Yoon et al. | |
| 2004/0006261 A1 | 1/2004 | Swedlow et al. | |
| 2004/0010188 A1 | 1/2004 | Wasserman et al. | |
| 2004/0024297 A1 | 2/2004 | Chen et al. | |
| 2004/0024326 A1 | 2/2004 | Yeo et al. | |
| 2004/0034293 A1 | 2/2004 | Kimball | |

(56) References Cited

U.S. PATENT DOCUMENTS

| | | |
|---|---|---|
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0197548 A1 | 9/2005 | Dietiker |
| 2005/0228248 A1 | 10/2005 | Dietiker |
| 2005/0254992 A1 | 11/2005 | Jenkins et al. |
| 2005/0267346 A1 | 12/2005 | Faber et al. |
| 2005/0277819 A1 | 12/2005 | Kiani et al. |
| 2005/0283059 A1 | 12/2005 | Iyer et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0224058 A1 | 10/2006 | Mannheimer |
| 2006/0229509 A1 | 10/2006 | Al-Ali et al. |
| 2006/0247501 A1 | 11/2006 | Ali |
| 2006/0258921 A1 | 11/2006 | Addison et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073126 A1 | 3/2007 | Raridan, Jr. |
| 2007/0129613 A1 | 6/2007 | Rochester et al. |
| 2008/0316488 A1 | 12/2008 | Mao et al. |

FOREIGN PATENT DOCUMENTS

| | | |
|---|---|---|
| FR | 2685865 | 1/1992 |
| JP | 3245042 | 10/1991 |
| JP | 6269430 | 9/1994 |
| JP | 7001273 | 1/1995 |
| JP | 2004261364 | 9/2004 |
| WO | WO8909566 | 10/1989 |
| WO | WO9001293 | 2/1990 |
| WO | WO9309711 | 5/1993 |
| WO | WO9502358 | 1/1995 |

OTHER PUBLICATIONS

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Lopez-Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Lopez-Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 1.

Pujary, C., et al.; "Photodetector Size Considerations in the Design of a Noninvasive Reflectance Pulse Oximeter for Telemedicine Applications," *IEEE*, pp. 148-149 (2003).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Odagiri, Y.; "Pulse Wave Measuring Device," *Micromechatronics*, vol. 42, No. 3, pp. 6-11 (undated) (Article in Japanese—contains English summary of article).

\* cited by examiner

MEDICAL SENSOR AND TECHNIQUE FOR USING THE SAME

BACKGROUND

The present disclosure relates generally to medical devices and, more particularly, to sensors used for sensing physiological parameters of a patient.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

The quality of the pulse oximetry measurement depends in part on the concentration of arterial blood relative to other tissue structures in the portion of the tissue illuminated by the sensor and in part on the magnitude of the pulsatile changes in the blood. Patient tissue variability and sensor placement variability can cause interference in the resulting pulse oximeter measurements. This variability stems, in part, from the heterogeneity of the tissue structure and vasculature within any specific sample of tissue and, in particular, the moving and pulsing structures, e.g., the arteries, within the tissue that non-linearly contribute to the optical density of the probed tissue bed.

BRIEF DESCRIPTION OF THE DRAWINGS

Advantages of the disclosure may become apparent upon reading the following detailed description and upon reference to the drawings in which.

DETAILED DESCRIPTION

One or more embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Typically, a pulse oximetry sensor employs a light source that shines photons of light on the tissue. The photons travel through the tissue and are variously transmitted, scattered, reflected, or absorbed. The photon distribution of the light depends in part on the physical structures of the tissue, including the pulsatile components, and may vary significantly within a single patient's tissue. Accordingly, simply shifting the placement of a sensor on the tissue by as little as a few millimeters, and therefore changing the paths by which the photons travel, can result in changes in the measured blood oxygen saturation of a few percent.

To address these concerns, it would be desirable to provide sensors and systems for pulse oximetry or other applications utilizing spectrophotometry that are capable of changing or adapting the optical components of the sensor to achieve improved signal strength and decreased interference from tissue variability. Sensors with adaptive optical components may provide improved measurements by adapting the emitted light to a light intensity profile that is associated with signal optimization. For example, an adaptive light emitter may be capable of emitting an increased intensity of light into a particular tissue region that has better perfusion and may be associated with an improved signal. Similarly, such an adaptive emitter may direct light away from regions of the tissue with surface discoloration or anatomical structures that may absorb light and result in decreased signal strength. In addition, sensors with adaptive optical components may also adapt the light detecting elements of the sensor to detect only light within certain wavelength or within a certain distribution profile associated with improved signals.

Figure 1:
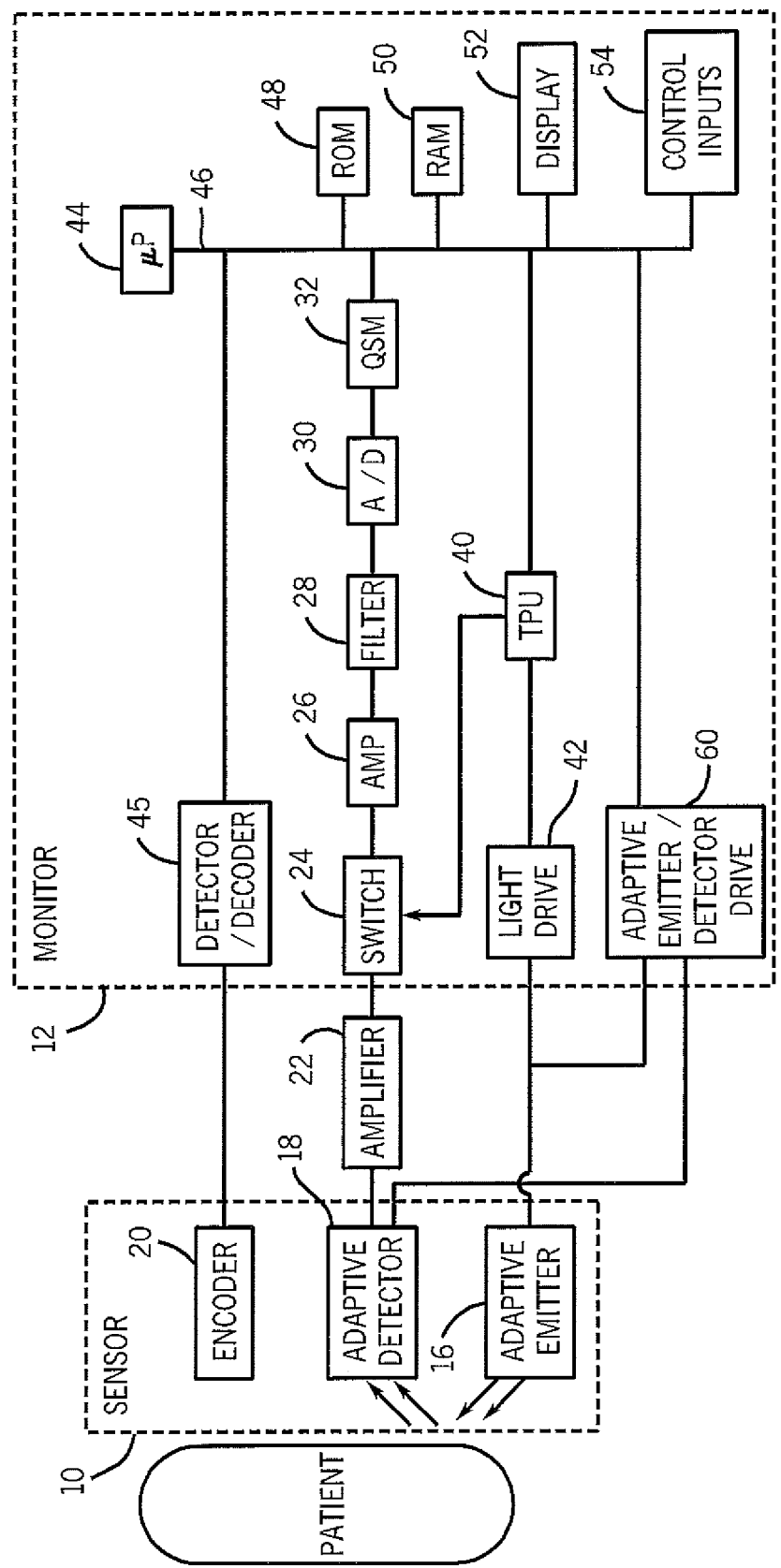
FIG. 1 is a block diagram of an exemplary medical sensor system.

A sensor including one or more adaptive emitters and/or adaptive detectors as provided herein and illustrated generically as a sensor 10, may be used in conjunction with a medical monitor 12, as illustrated in FIG. 1. A block diagram of an embodiment of a medical monitor 12 that may be configured to implement embodiments of the present disclosure. In an embodiment, the sensor 10 may be connected a pulse oximetry monitor, such as those available from Nellcor Puritan Bennett LLC. Light from adaptive emitter 16 may pass into a blood perfused tissue, and may be scattered, and then detected by adaptive detector 18. A sensor 10 containing an adaptive emitter 16 and an adaptive detector 18 may also contain an encoder 20, which may be capable of providing signals indicative of the wavelength(s) of emitter 16 to allow the oximeter to select appropriate calibration coefficients for calculating oxygen saturation. The encoder 20 may, in an embodiment, be a resistor.

In an embodiment, the monitor 12 may include a microprocessor 44 coupled to an internal bus 46. Also connected to the bus may be a RAM memory 50 and a display 52. A time processing unit (TPU) 40 may provide timing control signals to light drive circuitry 42, which controls when the adaptive emitter 16 is activated, and if multiple light sources are used, the multiplexed timing for the different light sources. TPU 40 may also control the gating-in of signals from adaptive detector 18 through an amplifier 22 and a switching circuit 24. These signals are sampled at the proper time, depending at least in part upon which of multiple light sources is activated, if multiple light sources are used. The received signal from the adaptive detector 18 may be passed through an amplifier 26, a low pass filter 28, and/or an analog-to-digital converter 30. The digital data may then be stored in a queued serial module (QSM) 32, for later downloading to RAM 50 as QSM 32 fills up. In an embodiment, there may be multiple parallel paths of separate amplifier, filter, and A/D converters for multiple light wavelengths or spectra received.

In an embodiment of a two-wavelength system, the particular set of coefficients chosen for any pail of wavelength spectra may be determined by a value indicated by the encoder 20 corresponding to a particular light source in a particular sensor 10. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 54. Control inputs 54 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter. In an embodiment, based at least in part upon the received signals corresponding to the light received by adaptive detector 18, microprocessor 44 may calculate the oxygen saturation using various algorithms. These algorithms may require coefficients, which may be empirically determined, and may correspond to the wavelengths of light used. The algorithms may be stored in a ROM 48 and accessed and operated according to microprocessor 44 instructions.

In one embodiment, the monitor 12 includes a separate drive 60 for the adaptive components of the adaptive emitter 16 and/or adaptive detector 18. While the light drive 42 may control a light source portion of the adaptive emitter 16, such as a light emitting diode, the adaptive drive 60 may control microelectromechanical portions of the adaptive optical components. In one embodiment, the adaptive drive 60 may direct certain microelectromechanical portions of a digital light processing array to independently orient in specified directions to control the directions and/or focus of emitted light and thereby direct the adaptive emitter 16 to produce a certain light intensity profile on the patient's tissue. In another embodiment, the adaptive drive 60 may direct application of voltage across portions of a liquid lens to change the curvature, and thus the optical properties, of the lens. In an embodiment, such a device may include a code or other identification parameter that may allow the monitor 12 to select an appropriate software or hardware instruction set for processing the signal and/or instructions for handling the adaptive emitter 16 and/or the adaptive detector 18. In an embodiment, the adaptive drive 60 may also be located on the sensor 10 or may be located in a sensor's electrical connector, such as a cable.

In an embodiment, the microprocessor 44 may provide instructions for calibrating a sensor 10 based on signals from the adaptive detector 18. For example, after a sensor is applied to a patient's tissue, a monitor 12 may initiate a calibration sweep of the optical components by directing the adaptive emitter 16 and/or the adaptive detector 18 to run through various configurations. The detected signals may be then processed or subjected to quality metrics (such as those provided in U.S. Pat. No. 7,194,293, to Baker, which is incorporated by reference in its entirety herein for all purposes) to determine which configuration has improved signal to noise ratios in the detected signal. For example, the signal from each configuration may be subjected to quality metrics to determine the best adapted configuration of the adaptive emitter 16, adaptive detector, 18, or a combination of both. In an embodiment, the calibration includes a sweep through a preprogrammed set of optical configurations. A "best quality" configuration may be determined, and the sensor 10 may be directed to improve upon the best quality configuration by adaptive learning routines that initiate iterative improvements of the best quality configuration. In such a manner, a monitor and/or sensor may adapt an emitter 16 and a detector 18 to each individual patient. In one embodiment, the calibration sweep may be repeated periodically to update the calibration and account for subtle movements of the sensor on the patient's skin and/or clinical changes in the patient's condition that may affect tissue hydration, which in turn may influence the photon distribution.

In an embodiment, certain configurations of the adaptive optical components may be associated with certain patient characteristics and/or tissue sites. For example, certain configurations of the adaptive optical components may show empirical improvements in signal quality when a sensor 10 is associated with an ear, digit, or forehead. A user may select the tissue site of the sensor placement, and the adaptive drive 60 may adjust the configuration of the adaptive optical components accordingly. In another embodiment, specific configurations of the adaptive optical components may be associated with patients certain skin colors as determined by, for example, Fitzpatrick skin color types. A monitor 12 may be adapted to allow a user to select a patient skin color and may subsequently provide instructions through the adaptive drive 60 to the adaptive optical elements.

In an embodiment, the adaptive optical components may be used to map the tissue structure to provide an indication to a healthcare provider about tissue structures that may be associated with signal quality changes. For example, a sensor 10 may "sweep" a tissue area by changing the configuration of the adaptive optical components and processing the detected signal Signals characteristic of large anatomic structures, such as bone or tissue masses, may be indicated to a healthcare provider. In addition, the information from the "sweeps" of the tissue may be used to reconstruct a tomographic image of the tissue properties below the surface using a variety of wavelengths and configurations of the source and receiver adaptive optical elements. These tomographic techniques are typically referred to as Diffuse Optical Tomography or Photon Migration Imaging.

Figure 2:
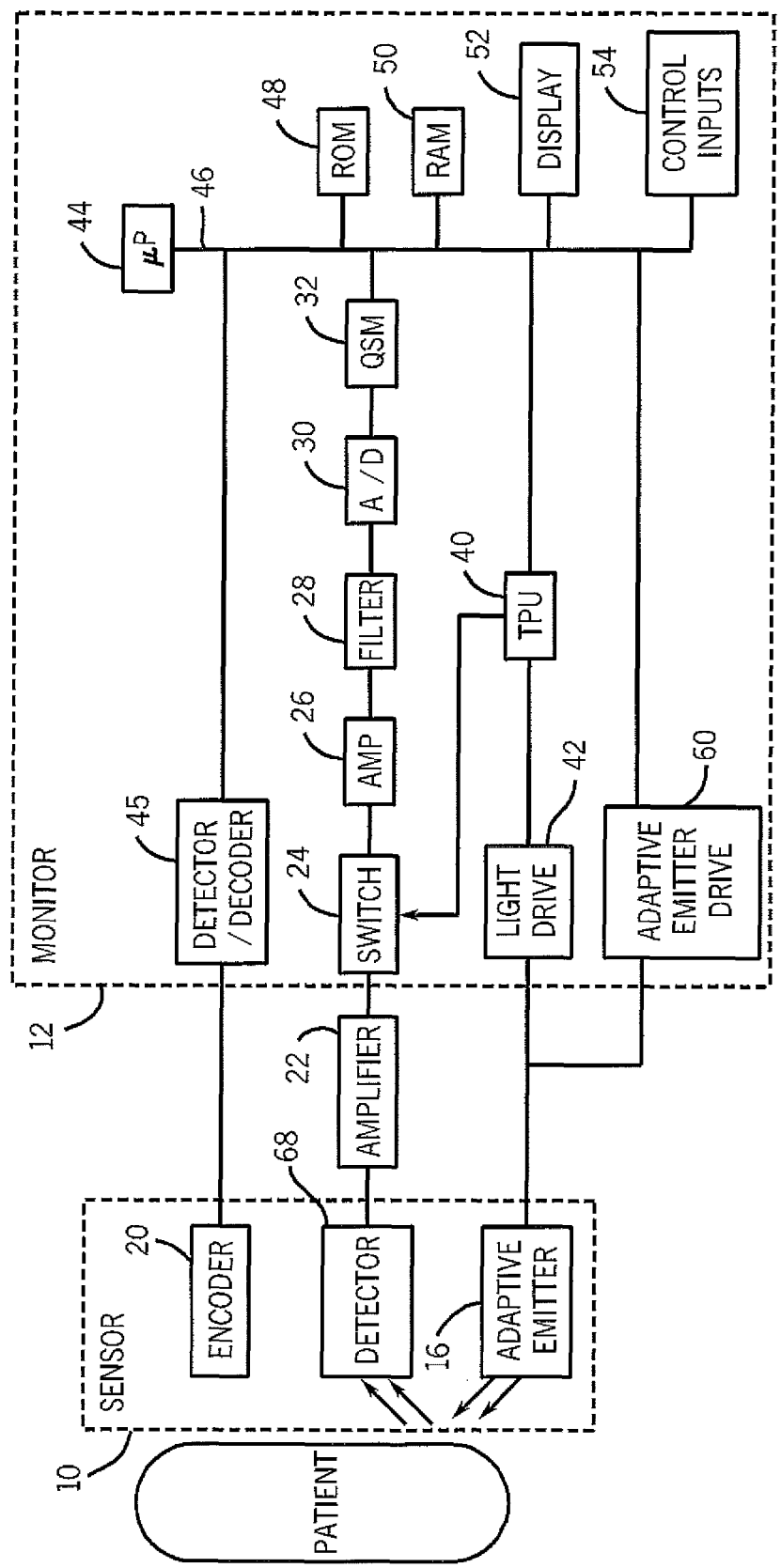
FIG. 2 is a block diagram of an exemplary medical sensor system.
Figure 3:
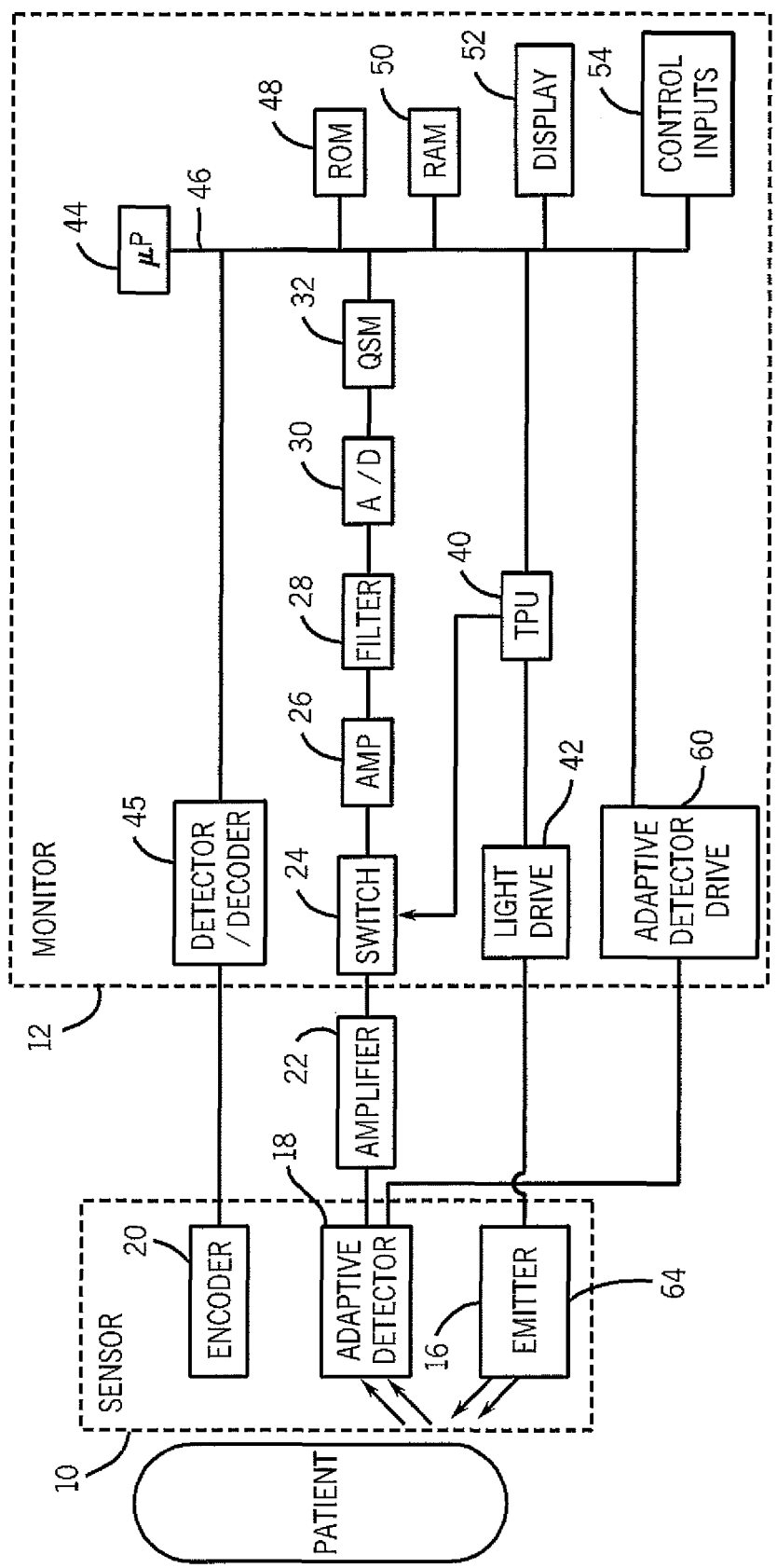
FIG. 3 is a block diagram of an exemplary medical sensor system.

In certain embodiments, such as those illustrated in FIG. 2 and FIG. 3, a sensor 10 may include a combination of adaptive and nonadaptive optical components. For example, FIG. 2 shows a sensor 10 with an adaptive emitter 16 coupled to a standard detector 68, such as a photodetector. In such an embodiment, the adaptive drive 60 may be coupled to the emitter 16. Alternatively, FIG. 3 shows an embodiment in which a light emitter 64 may be coupled to an adaptive detector 18. In the depicted embodiment, the adaptive drive 60 is coupled to the detector 18.

Figure 4:
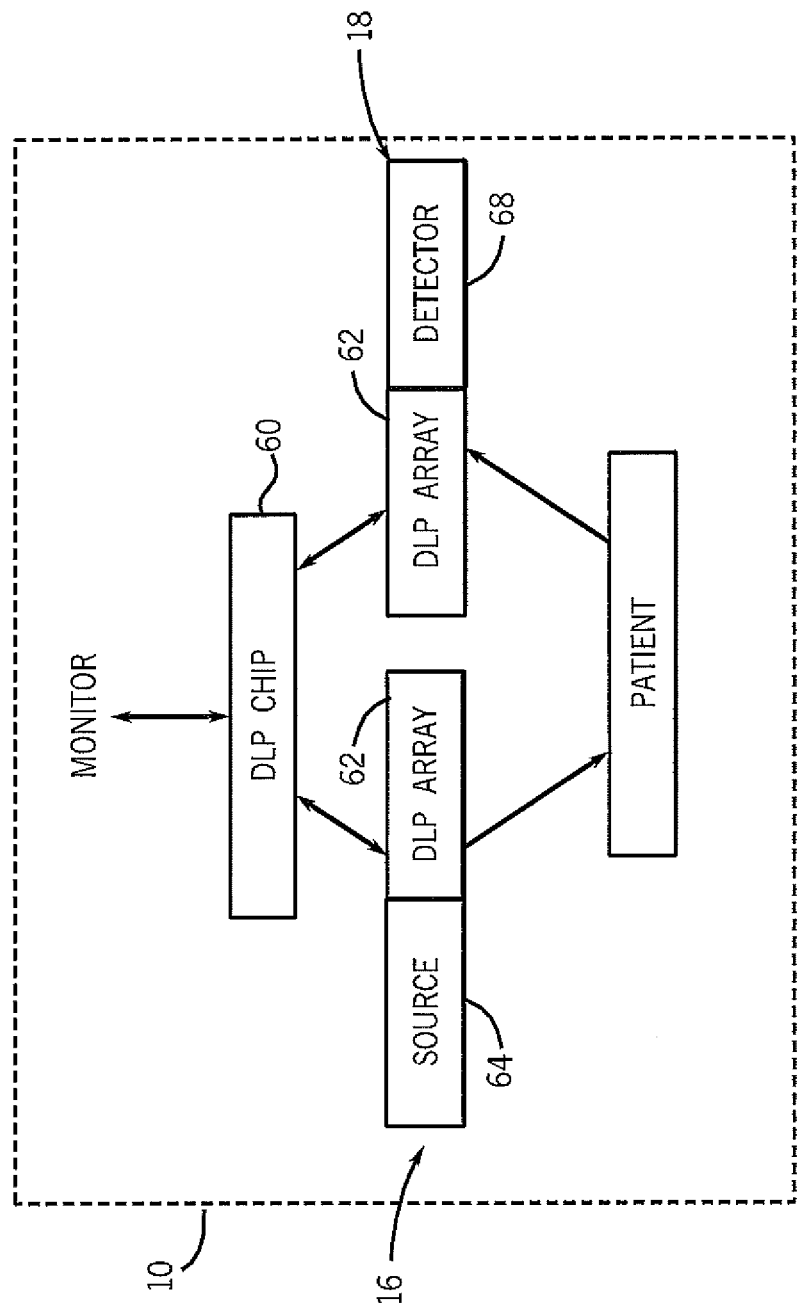
FIG. 4 illustrates a block diagram of an exemplary medical sensor.

FIG. 4 shows a block diagram of a sensor 10 that includes an adaptive emitter 16 and an adaptive detector 18, according to an embodiment. As depicted, the adaptive components of the emitter 16 and detector 18 may include digital light processing arrays 62 coupled to either a light source 64 and/or a light detector 68. The sensor 10 may include a digital light processing chip 60 with functionality to respond to processor instructions from a downstream monitor to control the microelectromechanical portions of the digital light processing arrays 62. In other embodiments, the digital light processing chip 60 may be provided on a monitor 20 and a control signal transmitted from the digital light processing chip 60 to the digital light processing arrays 62.

In an embodiment, the adaptive emitter 16 includes a light source 64, and the adaptive detector includes a light detector 68. The light source 64 may be adapted to be coupled with the digital light processing array 62 to allow the digital light processing array 62 to direct the path of the emitted light onto the tissue. The light detector may be adapted to be coupled with the digital light processing array 62 to allow the digital light processing array 62 to direct the path of the light that has passed through the tissue to impinge the light detector 68.

In an embodiment, light source 64 may be one or more light emitting diodes adapted to transmit one or more wavelengths of light in the red to infrared range, and the light detector 68 may include one or more detectors selected to receive light in the range or ranges emitted from the adaptive emitter 16. Alternatively, the tight source 64 may also be a laser diode or a vertical cavity surface emitting laser (VCSEL). A light source 64 may also include optical fiber sensing elements. The light source 64 may include a broadband or "white light" source, in which case the adaptive detector could include any of a variety of elements for selecting specific wavelengths, such as reflective or refractive elements or interferometers. Alternatively, a sensor 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects.

In an embodiment of a pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "elight" may refer to one or more of radio, microwave, millimeter wave, infrared, visible, ultraviolet, gamma ray or X-ray, and/or electromagnetic radiation, and may also include any wavelength within the radio, microwave, infrared, visible, ultraviolet, or X-ray spectra.

In an embodiment, the digital light processing array 62 may include a digital micromirrors disposed on a substrate (see FIG. 5), and any suitable focusing and/or collimating optics. For example, the digital light processing array 62 may include a lens or series of lenses designed to direct light from the light source 64 to digital micromirrors.

The digital light processing array 62 may also include a lens or series of lenses designed to focus light from the digital micromirrors onto a patient's tissue.

Figure 5:
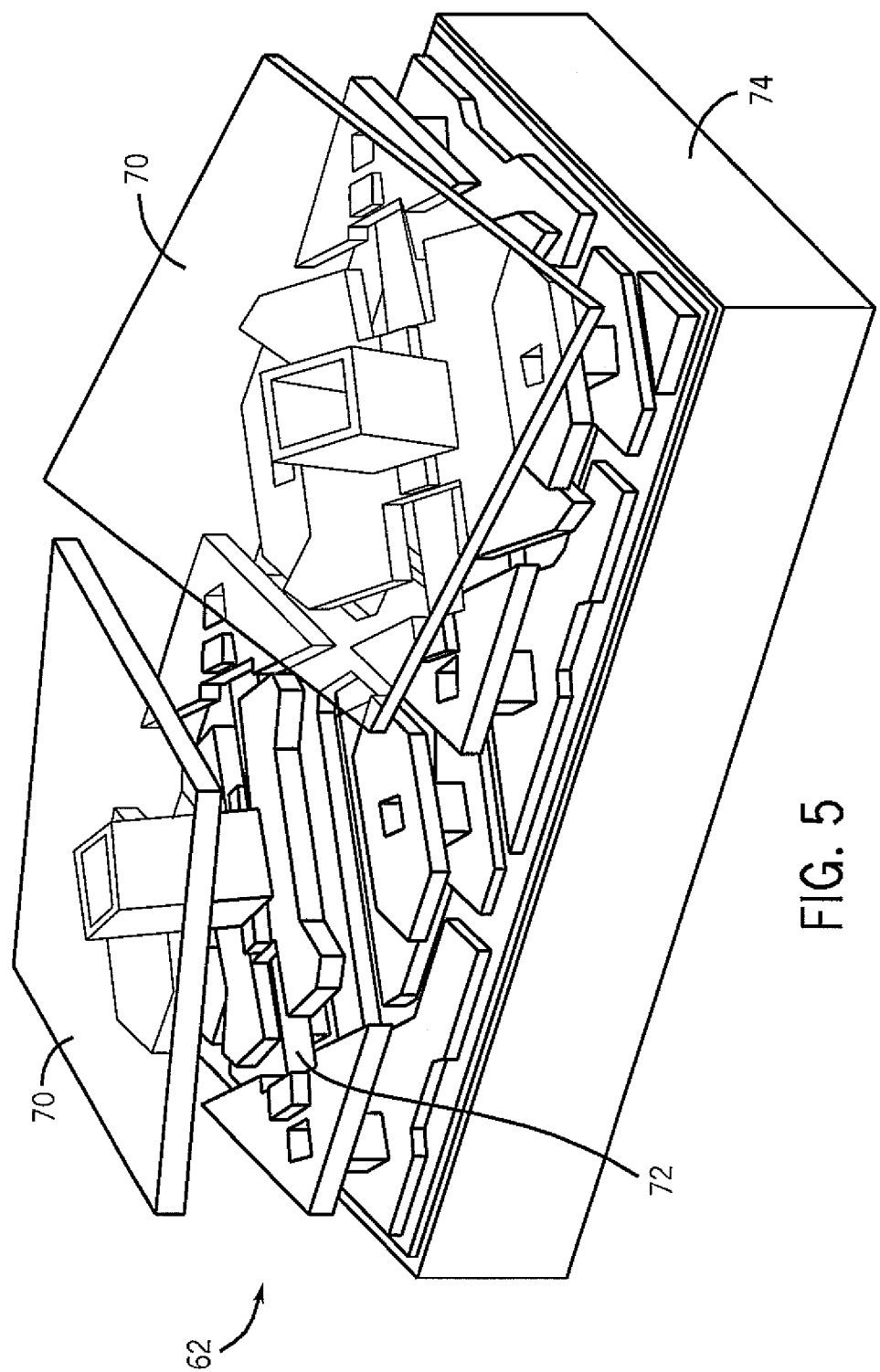
FIG. 5 is a schematic view of an exemplary microelectromechanical assembly for digital light projection that may be incorporated into a sensor as provided herein.

FIG. 5 is a schematic view of an embodiment of a portion of a digital light processing array 62, such as the digital light processing systems available from Texas Instruments (Dallas, Tex.) that may be incorporated into an adaptive emitter 16 or an adaptive detector 18. Such an array 62 may include thousands of micromirrors 70. The array 62 may also include a controlling substrate 74, such as a CMOS substrate, and a torsion hinge 72 that controls the motion of the micromirrors 70.

In one embodiment, each mirror portion 70 is able to move into two states, +10 degrees for "on" or −10 degrees for "off," and thereby control the direction of light hitting the mirror 70. Essentially, when a mirror 70 rotates via the hinge 72 to its on state, light from a light source is projected through the focusing optics and when the mirror 70 rotates via the hinge 72 to its off state, light from a light source 64 may projected away from the focusing optics. A digital signal may address the controlling substrate 74 below each mirror portion 70 of the digital micromirror device. Responding to this electrical signal, each mirror 70 interacts with incident light from the light source as described above, with the input signal controlling how long each mirror stays in either the on or off state.

Figure 6:
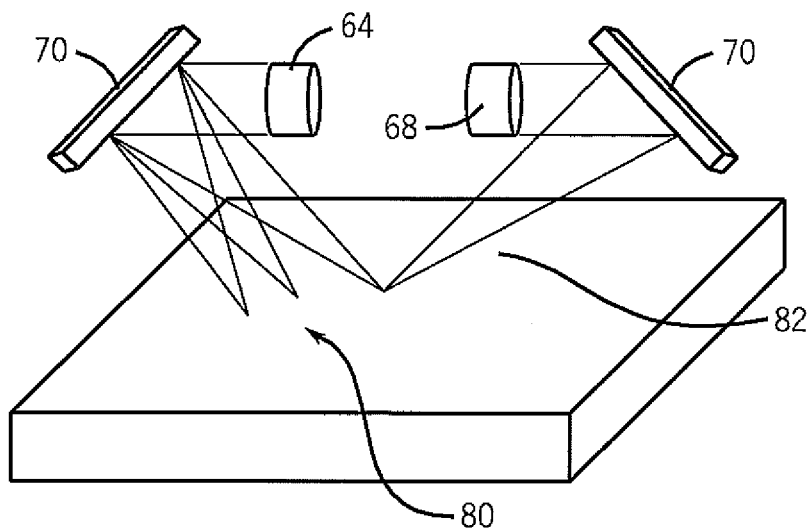
FIG. 6 is a schematic view of an exemplary optical source and adaptive detector interacting with a digital light projection assembly to shine light on a patient's tissue and detect the emitted light.

In an embodiment, as shown in FIG. 6, in operation, a sensor 10 with an adaptive emitter 16 and an adaptive detector 18 may control the light emitted from the light source 64 by directing the light into particular distributions onto the tissue 82. For example, emitted light 80 may be directed by the mirror 70 to certain portions of the tissue 82 and cancelled out in other portions. In addition, the adaptive detector 18 may be configured to only detect certain wavelengths of light, or light reflected back from certain portions of the tissue. By changing configurations, the adaptive detector 18 may act as a light filter or grating. In this manner, the sensor 10 may utilize a broadband light source 64 and employ the adaptive detector 18 to filter out the undesirable wavelength ranges. In such an embodiment, a sensor 10 may be able to change from a pulse oximetry sensor to a water fraction sensor by driving the adaptive detector 18 to change configurations as appropriate to filter out different wavelength ranges.

In one embodiment, the configured photon intensity distributions of the adaptive optical components may also be achieved by employing liquid lens technology in the adaptive optical components, see for example, U.S. Pat. No. 6,369,954 to Berge et al. and U.S. Pat. No. 6,665,127 to Bao et al., the specifications of which are hereby incorporated by reference herein for all purposes. By applying an external voltage to the liquid, the surface profile of the liquid may be tuned because of the contact angle change. As a result, the focal length of the liquid lens may be varied. In one embodiment, a tunable-focus liquid lens may be used that employs pressure induced liquid redistribution. The liquid lens may be composed of a flat cell and a liquid. The rigid flat cell has two non-overlapping holes that are sealed with elastic membranes. One membrane is adhered on the outer surface of a substrate and the other is adhered on the inner surface of another substrate. The liquid is fully filled in the cell chamber and sealed. Initially the two membranes are flat, so no focusing effect takes place. Squeezing the outside membrane inward by an actuator or other electromechanical means will redistribute the liquid rapidly, thus the inside membrane will swell outward and change the focus of the lens.

Figure 7:
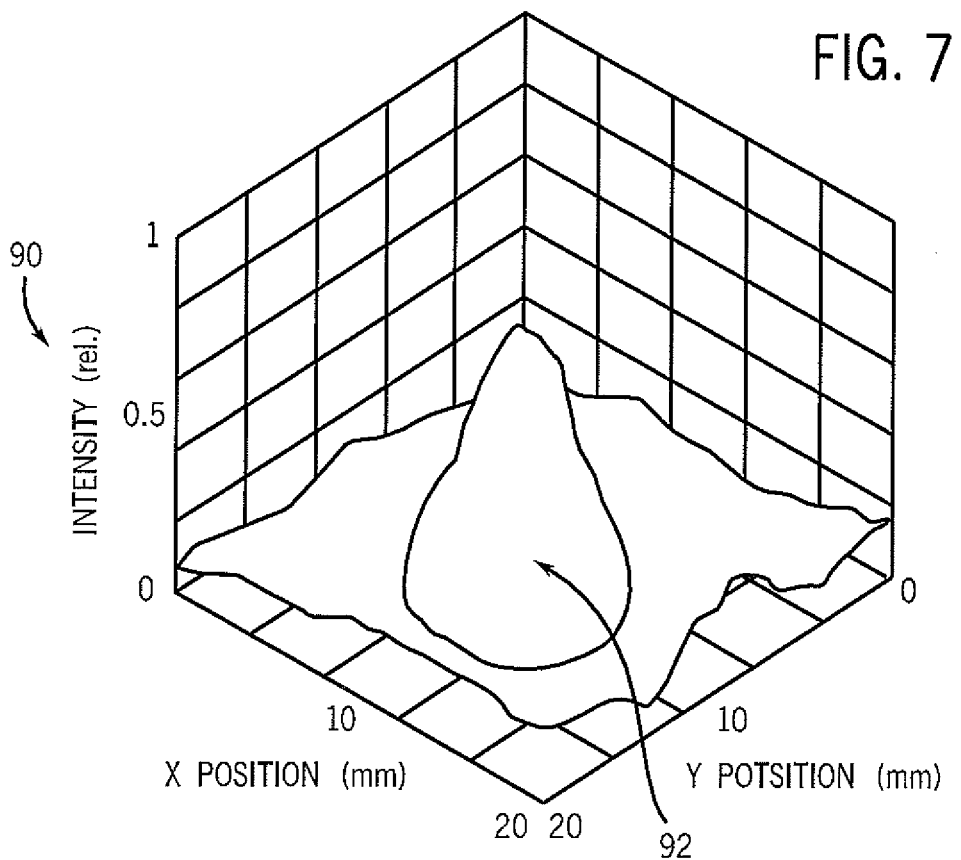
FIG. 7 is an exemplary photon intensity distribution that may be emitted by an adaptive emitter as provided herein.

FIG. 7 shows an exemplary photon intensity distribution 92 that may be emitted by an adaptive emitter 16 onto a patient's tissue, according to an embodiment. Once the sensor 10 is suitably applied to the tissue, the adaptive emitter 16 transmits the selected wavelength(s) of light onto and into the tissue. The intensity 90 with which the photons of light impact the tissue at various locations along the tissue surface may mapped to represent the photon intensity distribution. The exemplary distribution 92, with a central peak fading at a substantially equal rate at all sides, may be similar to the effect of a light source shining straight down on the tissue. The adaptive emitter 16 may replicate the effect of other types of light sources, or may create photon intensity distributions with complex patterns that are difficult to achieve with conventional light sources. In other embodiments, the photon intensity distribution may have several peaks and valleys or may be substantially flat, i.e., uniform, over the area of exposure.

Figure 8:
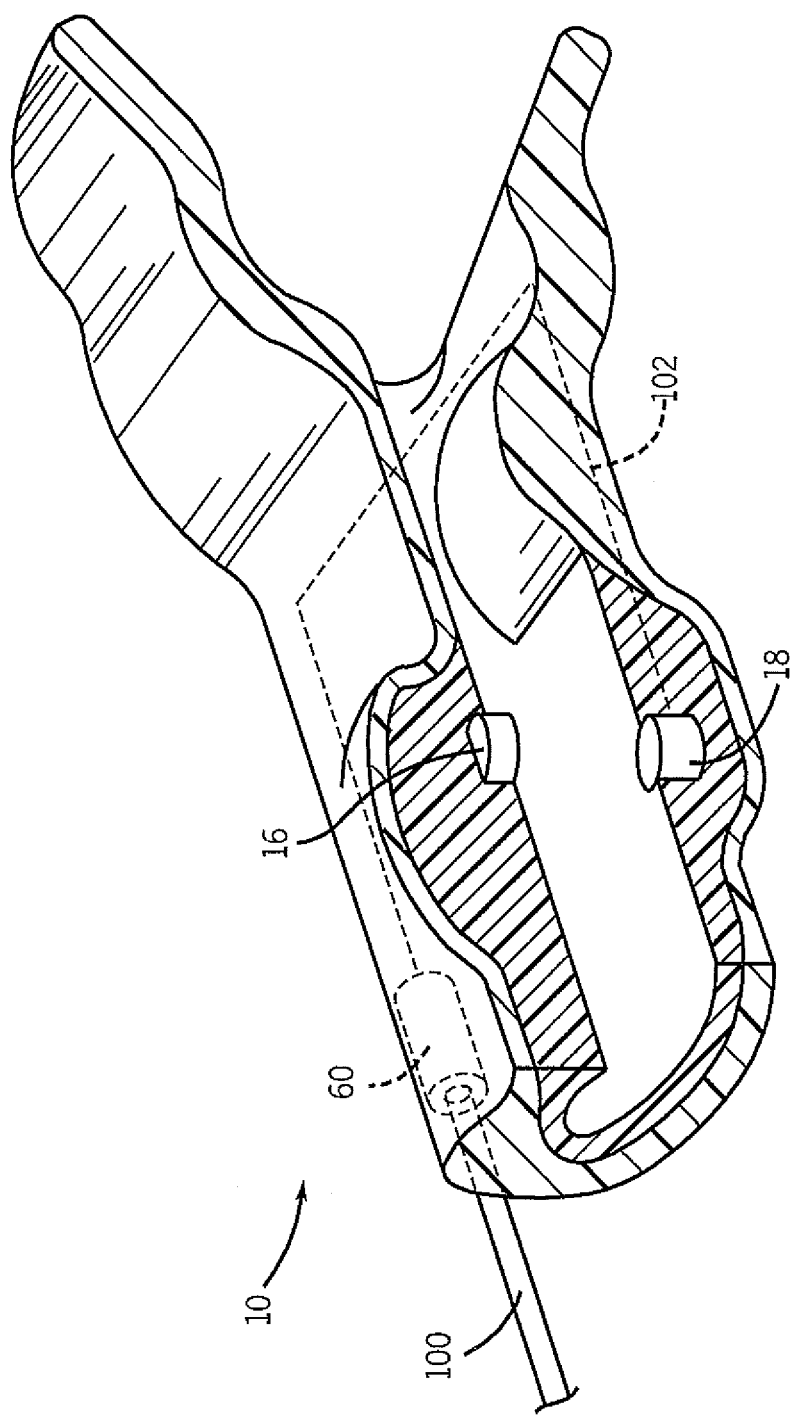
FIG. 8 is a cross-sectional view of an exemplary medical sensor.

In the embodiment shown in FIG. 8, the adaptive emitter 16 and the adaptive detector 18 may be disposed on a sensor body 102, which may be made of any suitable material, such as plastic, foam, woven material, or paper. In certain embodiments, the sensor body 102 may be in the form of a bandage-style structure or a clip-style structure. In one embodiment, the sensor body 102 may be a molded reusable structure with recesses into which the adaptive emitter 16 and the adaptive detector 18 may be mounted. In the depicted embodiments, the sensor 10 is coupled to a cable 100 that is responsible for transmitting signals to and from the adaptive emitter 16 and adaptive detector 18 of the sensor 10 to the monitor 12.

In an embodiment) the sensor 10 may include a "transmission type" sensor, as shown in FIG. 8. Transmission type sensors may include an emitter and detector, such as an adaptive emitter 16 and/or adaptive detector 18, that are typically placed on opposing sides of the sensor site. If the sensor site is a fingertip, for example, the sensor 10 is positioned over the patient's fingertip such that the adaptive emitter 16 and adaptive detector 18 lie on either side of the patient's nail bed. In other words, the sensor 10 is positioned so that the adaptive emitter 16 is located on the patient's fingernail and the adaptive detector 18 is located 180° opposite the adaptive emitter 16 on the patient's finger pad. During operation, the adaptive emitter 16 shines one or more wavelengths of light through the patient's fingertip and the light received by the adaptive detector 18 is processed to determine various physiological characteristics of the patient. In each of the embodiments discussed herein, it should be understood that the locations of the adaptive emitter 16 and the adaptive detector 18 may be exchanged. For example, the adaptive detector 18 may be located at the top of the finger and the adaptive emitter 16 may be located underneath the finger. In either arrangement, the sensor 10 will perform in substantially the same manner.

In an embodiment, reflectance type sensors also operate by emitting light into the tissue and detecting the light that is transmitted and scattered by the tissue. However, reflectance type sensors may include an adaptive emitter 16 and adaptive detector 18 that are typically placed on the same side of the sensor site. For example, a reflectance type sensor may be placed on a patient's fingertip or forehead such that the adaptive emitter 16 and adaptive detector 18 lie side-by-side. Reflectance type sensors detect light photons that are scattered back to the adaptive detector 18. A sensor 10 may also be a "transflectance" sensor, such as a sensor that may subtend a portion of a baby's heel.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may to cover all modifications, equivalents, and alternatives falling within the spirit and scope of the disclosure as defined by the following appended claims.

What is claimed is:

1. A monitoring system comprising:
a sensor capable of being operatively coupled to a medical monitor, the sensor comprising:
a sensor body capable of being applied to a patient's tissue;
an adaptive light emitting structure disposed on the sensor body and configured to emit light at a first wavelength, wherein the adaptive light emitting structure comprises a plurality of configurable elements configured to be independently addressed to change a path of the emitted light from at least one of the configurable elements relative to at least one other configurable element of the plurality of configurable elements and to change an intensity profile of light at the first wavelength emitted by the adaptive light emitting structure; and
a detector disposed on the sensor body and spaced apart from the adaptive light emitting structure, wherein the detector is capable of detecting at least a portion of the emitted light; and
a medical monitor comprising a processor, wherein the processor is configured to independently address the configurable elements of the adaptive light emitting element to change the path and the intensity profile of the emitted light.

2. The system, as set forth in claim 1, wherein the detector comprises an adaptive light detecting structure comprising a second plurality of configurable elements that can be independently addressed to change a location from which light is detected.

3. The system, as set forth in claim 1, wherein the configurable elements comprise micro electromechanical elements of a digital light processor array or a liquid lens assembly.

4. The system, as set forth in claim 1, comprising a processing chip or processing driver for the adaptive light emitting structure disposed in or on the sensor body, in or on an electrical connector extending from the sensor body, or in the monitor.

5. The system, as set forth in claim 1, wherein the sensor comprises a pulse oximetry sensor and the monitor comprises a pulse oximetry monitor.

6. The system, as set forth in claim 1, wherein a user may provide input to the processor that may be used to independently address the configurable elements of the adaptive light emitting element to change an orientation of the configurable elements relative to one another.

7. The system, as set forth in claim 1, wherein the processor is capable of changing a configuration of the configurable elements of the adaptive light emitting element relative to one another one or more times to calibrate the sensor.

8. The system, as set forth in claim 1, comprising a second adaptive light emitting structure disposed on the sensor body and configured to emit light at a second wavelength, wherein the second adaptive light emitting structure comprises a plurality of configurable elements that can be independently addressed to change an intensity profile of light at the second wavelength emitted by the plurality of configurable elements of the second adaptive light emitting structure.

9. The system, as set forth in claim 8, wherein the first wavelength is in a red wavelength range and the second wavelength is in the infrared wavelength range.

\* \* \* \* \*